US009605259B2

(12) United States Patent
Bennett

(10) Patent No.: US 9,605,259 B2
(45) Date of Patent: *Mar. 28, 2017

(54) COMPOUNDS AND METHODS FOR MODULATING PROTEIN EXPRESSION

(71) Applicant: Ionis Pharmaceuticals, Inc., Carlsbad, CA (US)

(72) Inventor: C. Frank Bennett, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,438

(22) Filed: Dec. 13, 2013

(65) Prior Publication Data
US 2014/0288291 A1 Sep. 25, 2014

Related U.S. Application Data

(63) Continuation of application No. 12/742,652, filed as application No. PCT/US2008/083448 on Nov. 13, 2008, now Pat. No. 8,637,478.

(60) Provisional application No. 60/987,759, filed on Nov. 13, 2007.

(51) Int. Cl.
*C07H 21/04* (2006.01)
*C12N 15/113* (2010.01)
*A61K 31/7115* (2006.01)
*C12N 15/11* (2006.01)

(52) U.S. Cl.
CPC ........ *C12N 15/113* (2013.01); *A61K 31/7115* (2013.01); *C12N 15/111* (2013.01); *C12N 2320/51* (2013.01)

(58) Field of Classification Search
CPC .................................................... C07H 21/04
See application file for complete search history.

(56) References Cited

U.S. PATENT DOCUMENTS

| | | |
|---|---|---|
| 5,013,830 A | 5/1991 | Ohtsuka et al. |
| 5,149,797 A | 9/1992 | Pederson et al. |
| 5,220,007 A | 6/1993 | Pederson et al. |
| 5,256,775 A | 10/1993 | Froehler |
| 5,366,878 A | 11/1994 | Pederson et al. |
| 5,403,711 A | 4/1995 | Walder et al. |
| 5,491,133 A | 2/1996 | Walder et al. |
| 5,565,350 A | 10/1996 | Kmiec |
| 5,623,065 A | 4/1997 | Cook et al. |
| 5,627,274 A | 5/1997 | Kole et al. |
| 5,652,355 A | 7/1997 | Metelev et al. |
| 5,652,356 A | 7/1997 | Agrawal |
| 5,665,593 A | 9/1997 | Kole et al. |
| 5,700,922 A | 12/1997 | Cook |
| 5,916,808 A | 6/1999 | Kole et al. |
| 5,976,879 A | 11/1999 | Kole et al. |
| 6,172,216 B1 | 1/2001 | Bennett et al. |
| 6,210,892 B1 | 4/2001 | Bennett et al. |
| 6,214,986 B1 | 4/2001 | Bennett et al. |
| 7,435,914 B2 | 10/2008 | Cheng |
| 2003/0143732 A1 | 7/2003 | Fosnaugh et al. |
| 2004/0063618 A1 | 4/2004 | Manoharan |
| 2004/0162259 A1 | 8/2004 | Wedel et al. |
| 2005/0054836 A1 | 3/2005 | Krainer et al. |
| 2005/0074801 A1 | 4/2005 | Monia et al. |
| 2005/0182005 A1 | 8/2005 | Tuschl et al. |
| 2006/0172962 A1 | 8/2006 | Vickers et al. |
| 2007/0105807 A1 | 5/2007 | Sazani et al. |
| 2007/0123484 A1 | 5/2007 | Bhat et al. |
| 2007/0166734 A1 | 7/2007 | Bhat et al. |
| 2007/0179109 A1 | 8/2007 | Bhat et al. |

FOREIGN PATENT DOCUMENTS

| | | |
|---|---|---|
| EP | 1469009 | 10/2004 |
| WO | WO 92/03568 | 3/1992 |
| WO | WO 2005/013901 | 2/2005 |
| WO | WO 2005/121370 | 12/2005 |
| WO | WO 2006/091233 | 8/2006 |
| WO | WO 2006/119137 | 11/2006 |
| WO | WO 2007/002390 | 1/2007 |
| WO | WO 2007/021896 | 2/2007 |
| WO | WO 2007/028065 | 3/2007 |
| WO | WO 2007/047913 | 4/2007 |
| WO | WO 2007/090073 | 8/2007 |
| WO | WO 2008/094945 | 8/2008 |

OTHER PUBLICATIONS

Altmann et al., "Second Generation of Antisense Oligonucleotides: From Nuclease Resistance to Biological Efficacy in Animals" Chimia (1996) 50:168-176.
Altmann et al., "Second-generation antisense oligonucleotides: structure-activity relationships and the design of improved signal-transduction inhibitors" Biochem. Soc. Trans. (1996) 24:630-637.
Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides & Nucleotides (1997) 16:917-926.
Baker et al., "2'-O-(2-Methoxy) ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.
Crooke et al., "Kinetic Characteristics of *Escherichia coli* Rnase H1: Cleavage of Various Antisense Oligonucleotide-RNA Duplexes" Biochemical Journal (1995) 312(2):599-608.
Davis et al., "Improved targeting of miRNA with antisense oligonucleotides" Nucleic Acids Research (2006) 34(8):2294-2304.
Esau et al., "miR-122 regulation of lipid metabolism revealed by in vivo antisense targeting" Cell Metabolism (2006) 3(2):87-98.
Hua et al., "Enhancement of SMN2 Exon 7 Inclusion by Antisense Oligonucleotides Targeting the Exon" PLoS Biol (2007) 5(4):e73.

(Continued)

*Primary Examiner* — Kimberly Chong
(74) *Attorney, Agent, or Firm* — Ionis Pharmaceuticals, Inc. Patent Dept.

(57) ABSTRACT

The present invention provides compounds and methods for modulating expression of a protein, including, but not limited to, modulating splicing of a pre-mRNA to modulate the amount of one or more variants of a protein.

20 Claims, No Drawings

(56) References Cited

OTHER PUBLICATIONS

Kawasaki et al., "Uniformly Modified 2'-Deoxy-2'-fluoro Phosphorothioate Oligonucleotides as Nuclease-Resistant Antisense Compounds with High Affinity and Specificity for RNA Targets" J. Med. Chem. (1993) 36(7):831-841.

Lok et al., "Potent Gene-Specific Inhibitory Properties of Mixed-Backbone Antisense Oligonucleotides Comprised of 2'-Deoxy-2'-fluoro-D-arabinose and 2'-Deoxyribose Nucleotides" Biochemistry (2002) 41:3457-3467.

Martin, "Ein neuer Zugang zu 2'-O-Alkylribonucleosiden und Eigenschaften deren Oligonucleotide" Helv. Chim. Acta (1995) 78:486-504.

Sazani et al., "Systemically delivered antisense oligomers upregulate gene expression in mouse tissues" Nature Biotechnology (2002) 20(12):1228-1233.

Suwanmanee et al., "Restoration of human beta-globin gene expression in murine and human IVS2-654 thalassemic erythroid cells by free uptake of antisense oligonucleotides" Molecular Pharmacology (2002) 62(3):545-553.

Vickers et al., "Modification of MyD88 mRNA Splicing and Inhibition of IL-1β Signaling in Cell Culture and in Mice with a 2'-O-Methoxyethyl-Modified Oligonucleotide" J. Immunol. (2006) 176(6):3652-3661.

Wright et al., "Effective delivery of antisense peptide nucleic acid oligomers into cells by anthrax protective antigen" Biochemical and Biphysical Research Communications (2008) 376(1):200-205.

International Search Report for application PCT/US2008/083448 dated Oct. 30, 2009.

International Search Report for application PCT/US2007/061186 dated Jul. 23, 2007.

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
tgctattacc ttaacccaga        20

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 2
gctattacct taacccag        18

COMPOUNDS AND METHODS FOR MODULATING PROTEIN EXPRESSION

CROSS REFERENCED TO RELATED APPLICATIONS

This application is a continuation of U.S. patent application Ser. No. 12/742,652, filed Oct. 8, 2010, which is a U.S. National Phase filing under 35 U.S.C. §371 claiming priority to International Serial No. PCT/US2008/083448 filed Nov. 13, 2008, which claims priority to U.S. Provisional Application 60/987,759, filed Nov. 13, 2007 and U.S. Provisional Application 61/496,462, filed Jun. 13, 2011, each of which is incorporated herein by reference in its entirety.

SEQUENCE LISTING

The present application is being filed along with a Sequence Listing in electronic format. The Sequence Listing is provided as a file entitled CORE0077USC1SEQ.txt, created Dec. 13, 2013, which is 4.0 Kb in size. The information in the electronic format of the sequence listing is incorporated herein by reference in its entirety.

FIELD OF THE INVENTION

The present invention provides methods and compositions for modulating protein expression.

BACKGROUND OF THE INVENTION

Antisense compounds have been used to modulate target nucleic acids. Antisense compounds comprising a variety of modifications and motifs have been reported. In certain instances, such compounds are useful as research tools and as therapeutic agents. In certain instances antisense compounds have been shown to modulate protein expression by altering splicing of a pre-mRNA, by arresting translation and/or by interrupting poly-adenylation of a pre-mRNA.

SUMMARY OF THE INVENTION

In certain embodiments, provided herein are compounds and methods that modulate protein expression, including, but not limited to, modulation of splicing.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "nucleoside" means a glycosylamine comprising a nucleobase and a sugar. Nucleosides include, but are not limited to, naturally occurring nucleosides, abasic nucleosides, modified nucleosides, and nucleosides having mimetic bases and/or sugar groups.

As used herein, the term "nucleotide" refers to a glycosomine comprising a nucleobase and a sugar having a phosphate group covalently linked to the sugar. Nucleotides may be modified with any of a variety of substituents.

As used herein, the term "nucleobase" refers to the base portion of a nucleoside or nucleotide. A nucleobase may comprise any atom or group of atoms capable of hydrogen bonding to a base of another nucleic acid.

As used herein, the term "heterocyclic base moiety" refers to a nucleobase comprising a heterocycle.

As used herein, the term "oligomeric compound" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antidote compounds. In certain embodiments, oligomeric compounds comprise conjugate groups.

As used herein "oligonucleoside" refers to an oligonucleotide in which the internucleoside linkages do not contain a phosphorus atom.

As used herein, the term "oligonucleotide" refers to an oligomeric compound comprising a plurality of linked nucleosides. In certain embodiments, one or more nucleotides of an oligonucleotide is modified. In certain embodiments, an oligonucleotide comprises ribonucleic acid (RNA) or deoxyribonucleic acid (DNA). In certain embodiments, oligonucleotides are composed of naturally- and/or non-naturally-occurring nucleobases, sugars and covalent internucleoside linkages, and may further include non-nucleic acid conjugates.

As used herein "internucleoside linkage" refers to a covalent linkage between adjacent nucleosides.

As used herein "naturally occurring internucleoside linkage" refers to a 3' to 5' phosphodiester linkage.

As used herein, the term "antisense compound" refers to an oligomeric compound that is at least partially complementary to a target nucleic acid molecule to which it hybridizes. In certain embodiments, an antisense compound modulates (increases or decreases) expression or amount of a target nucleic acid. In certain embodiments, an antisense compound alters splicing of a target pre-mRNA resulting in a different splice variant. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

As used herein, the term "antisense oligonucleotide" refers to an antisense compound that is an oligonucleotide.

As used herein, the term "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids.

As used herein the term "detecting antisense activity" or "measuring antisense activity" means that a test for detecting or measuring antisense activity is performed on a particular sample and compared to that of a control sample. Such detection and/or measuring may include values of zero. Thus, if a test for detection of antisense activity results in a finding of no antisense activity (antisense activity of zero), the step of "detecting antisense activity" has nevertheless been performed.

As used herein, the term "splice altering activity" refers to a change in the ratio of one splice variant nucleic acid or splice variant protein product to another splice variant nucleic acid or splice variant protein product attributable to antisense activity.

As used herein, the term "detecting splice altering activity" or "measuring splice altering activity" means that a test for detecting or measuring splice altering activity is performed on a sample and compared to a control sample. Such detection and/or measuring may include values of zero. Thus, if a test for detection of antisense activity results in a finding of no splice altering activity (splice altering activity of zero), the step of "detecting splice altering activity" has nevertheless been performed.

As used herein the term "control sample" refers to a sample that has not been contacted with an antisense compound.

As used herein, the term "motif" refers to the pattern of unmodified and modified nucleotides in an oligomeric compound.

As used herein, the term "chimeric antisense oligomeric compound" refers to an antisense oligomeric compound, having at least one sugar, nucleobase or internucleoside linkage that is differentially modified as compared to at least on other sugar, nucleobase or internucleoside linkage within the same antisense oligomeric compound. The remainder of the sugars, nucleobases and internucleoside linkages can be independently modified or unmodified, the same or different.

As used herein, the term "chimeric antisense oligonucleotide" refers to an antisense oligonucleotide, having at least one sugar, nucleobase or internucleoside linkage that is differentially modified as compared to at least on other sugar, nucleobase or internucleoside linkage within the same antisense oligonucleotide. The remainder of the sugars, nucleobases and internucleoside linkages can be independently modified or unmodified, the same or different.

As used herein, the term "mixed-backbone oligomeric compound" refers to an oligomeric compound wherein at least one internucleoside linkage of the oligomeric compound is different from at least one other internucleoside linkage of the oligomeric compound.

As used herein, the term "target protein" refers to a protein, the modulation of which is desired.

As used herein, the term "target gene" refers to a gene encoding a target protein.

As used herein, the term "target nucleic acid" refers to any nucleic acid molecule the expression or activity of which is capable of being modulated by an antisense compound. Target nucleic acids include, but are not limited to, RNA (including, but not limited to pre-mRNA and mRNA or portions thereof) transcribed from DNA encoding a target protein, and also cDNA derived from such RNA, and miRNA.

For example, the target nucleic acid can be a cellular gene (or mRNA transcribed from the gene) whose expression is associated with a particular disorder or disease state, or a nucleic acid molecule from an infectious agent.

As used herein, the term "targeting" or "targeted to" refers to the association of an antisense compound to a particular target nucleic acid molecule or a particular region of nucleotides within a target nucleic acid molecule.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" means the pairing of complementary oligomeric compounds (e.g., an antisense compound and its target nucleic acid or an antidote to its antisense compound). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "designing" or "designed to" refer to the process of designing an oligomeric compound that specifically hybridizes with a selected nucleic acid molecule.

As used herein, the term "modulation" refers to a perturbation of amount or quality of a function or activity when compared to the function or activity prior to modulation. For example, modulation includes the change, either an increase (stimulation or induction) or a decrease (inhibition or reduction) in gene expression. As further example, modulation of expression can include perturbing splice site selection of pre-mRNA processing, resulting in a change in the amount of a particular splice-variant present compared to conditions that were not perturbed.

As used herein, the term "expression" refers to all the functions and steps by which a gene's coded information is converted into structures present and operating in a cell. Such structures include, but are not limited to the products of transcription and translation.

As used herein, "variant" refers to an alternative RNA transcript that can be produced from the same genomic region of DNA. Variants include, but are not limited to "pre-mRNA variants" which are transcripts produced from the same genomic DNA that differ from other transcripts produced from the same genomic DNA in either their start or stop position and contain both intronic and exonic sequence. Variants also include, but are not limited to, those with alternate splice junctions, or alternate initiation and termination codons.

As used herein, "high-affinity modified monomer" refers to a monomer having at least one modified nucleobase, internucleoside linkage or sugar moiety, when compared to naturally occurring monomers, such that the modification increases the affinity of an antisense compound comprising the high-affinity modified monomer to its target nucleic acid. High-affinity modifications include, but are not limited to, monomers (e.g., nucleosides and nucleotides) comprising 2'-modified sugars.

As used herein, the term "2'-modified" or "2'-substituted" means a sugar comprising substituent at the 2' position other than H or OH. 2'-modified monomers, include, but are not limited to, BNA's and monomers (e.g., nucleosides and nucleotides) with 2'-substituents, such as allyl, amino, azido, thio, O-allyl, O—C1-C10 alkyl, —OCF3, O—(CH2)2-O—CH3, 2'-O(CH2)2SCH3, O—(CH2)2-O—N(Rm)(Rn), or O—CH2-C(=O)—N(Rm)(Rn), where each Rm and Rn is, independently, H or substituted or unsubstituted C1-C10 alkyl. In certain embodiments, oligomeric compounds comprise a 2' modified monomer that does not have the formula 2'-O(CH2)nH, wherein n is one to six. In certain embodiments, oligomeric compounds comprise a 2' modified monomer that does not have the formula 2'-OCH3. In certain embodiments, oligomeric compounds comprise a 2' modified monomer that does not have the formula or, in the alternative, 2'-O(CH2)2OCH3.

As used herein, the term "bicyclic nucleic acid" or "BNA" or "bicyclic nucleoside" or "bicyclic nucleotide" refers to a nucleoside or nucleotide wherein the furanose portion of the nucleoside includes a bridge connecting two carbon atoms on the furanose ring, thereby forming a bicyclic ring system.

As used herein, unless otherwise indicated, the term "methyleneoxy BNA" alone refers to β-D-methyleneoxy BNA.

As used herein, the term "MOE" refers to a 2'-O-methoxyethyl substituent.

As used herein, the term "gapmer" refers to a chimeric oligomeric compound comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) in each wing are the same. In certain embodiments, the modification(s) in one wing are different from the modification(s) in the other wing. In certain embodiments, oligomeric compounds are gapmers having 2'-deoxynucleotides in the gap and nucleotides with high-affinity modifications in the wing.

As used herein, "different modifications" or "differently modified" refer to nucleosides or internucleoside linkages that have different nucleoside modifications or internucleoside linkages than one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides.

As used herein, the term "prodrug" refers to a therapeutic agent that is prepared in an inactive form that is converted to an active form (i.e., drug) within the body or cells thereof by the action of endogenous enzymes or other chemicals and/or conditions.

As used herein, the term "pharmaceutically acceptable salts" refers to salts of active compounds that retain the desired biological activity of the active compound and do not impart undesired toxicological effects thereto.

As used herein, the term "cap structure" or "terminal cap moiety" refers to chemical modifications, which have been incorporated at either terminus of an antisense compound.

As used herein, the term "prevention" refers to delaying or forestalling the onset or development of a condition or disease for a period of time from hours to days, preferably weeks to months.

As used herein, the term "amelioration" refers to a lessening of at least one activity or one indicator of the severity of a condition or disease. The severity of indicators may be determined by subjective or objective measures which are known to those skilled in the art.

As used herein, the term "treatment" refers to administering a composition of the invention to effect an alteration or improvement of the disease or condition. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

As used herein, the term "pharmaceutical agent" refers to a substance provides a therapeutic benefit when administered to a subject.

As used herein, the term "therapeutically effective amount" refers to an amount of a pharmaceutical agent that provides a therapeutic benefit to an animal.

As used herein, "administering" means providing a pharmaceutical agent to an animal, and includes, but is not limited to administering by a medical professional and self-administering.

As used herein, the term "pharmaceutical composition" refers to a mixture of substances suitable for administering to an individual. For example, a pharmaceutical composition may comprise an antisense oligonucleotide and a sterile aqueous solution.

As used herein, the term "animal" refers to a human or non-human animal, including, but not limited to, mice, rats, rabbits, dogs, cats, pigs, and non-human primates, including, but not limited to, monkeys and chimpanzees.

As used herein, the term "parenteral administration," refers to administration through injection or infusion. Parenteral administration includes, but is not limited to, subcutaneous administration, intravenous administration, or intramuscular administration.

As used herein, the term "subcutaneous administration" refers to administration just below the skin. "Intravenous administration" means administration into a vein.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

As used herein, the term "dosage unit" refers to a form in which a pharmaceutical agent is provided. In certain embodiments, a dosage unit is a vial comprising lyophilized antisense oligonucleotide. In certain embodiments, a dosage unit is a vial comprising reconstituted antisense oligonucleotide.

As used herein, the term "active pharmaceutical ingredient" refers to the substance in a pharmaceutical composition that provides a desired effect.

As used herein, the term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C1-C12 alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, the term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, the term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butyryl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, the term "aminoalkyl" as used herein, refers to an amino substituted alkyl radical. This term is meant to include C1-C12 alkyl groups having an amino substituent at any position and wherein the alkyl group attaches the aminoalkyl group to the parent molecule. The alkyl and/or amino portions of the aminoalkyl group can be further substituted with substituent groups.

As used herein, the term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

As used herein, the term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups. As used herein, the term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

As used herein, the terms "halo" and "halogen," as used herein, refer to an atom selected from fluorine, chlorine, bromine and iodine.

As used herein, the terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups.

As used herein, the terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

As used herein, the term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

As used herein, the terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

As used herein, the term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

As used herein, the term "mono or poly cyclic structure" as used in the present invention includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

As used herein, the term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, the term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

As used herein, the terms "substituent" and "substituent group," include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)Raa), carboxyl (—C(O)O-Raa), aliphatic groups, alicyclic groups, alkoxy, substituted oxo (—O-Raa), aryl, aralkyl, heterocyclic, heteroaryl, heteroarylalkyl, amino (—NRbbRcc), imino (=NRbb), amido (—C(O)NRbbRccor —N(Rbb)C(O)Raa), azido (—N3), nitro (—NO2), cyano (—CN), carbamido (—OC(O)NRbbRcc or —N(Rbb)C(O)ORaa), ureido (—N(Rbb)C(O)NRbbRcc), thioureido (—N(Rbb)C—(S)NRbbRcc), guanidinyl (—N(Rbb)C(=NRbb)NRbbRcc), amidinyl (—C(=NRbb)NRbbRcc or —N(Rbb)C(NRbb)Raa), thiol (—SRbb), sulfinyl (—S(O)Rbb), sulfonyl (—S(O) 2Rbb), sulfonamidyl (—S(O)2NRbbRcc or —N(Rbb)S(O) 2Rbb) and conjugate groups. Wherein each Rau, Rbb and Rcc is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

A "stabilizing modification" means providing enhanced stability, in the presence of nucleases, relative to that provided by 2'-deoxynucleosides linked by phosphodiester internucleoside linkages. Thus, such modifications provide "enhanced nuclease stability" to oligomeric compounds. Stabilizing modifications include at least stabilizing nucleosides and stabilizing internucleoside linkage groups.

The term "stability enhancing nucleoside" or "stabilizing nucleoside" is meant to include all manner of nucleosides known to those skilled in the art to provide enhanced nuclease stability of oligomeric compounds. In one embodiment, stabilizing nucleosides can be 2'-modified nucleosides. Examples of such stability enhancing 2'-modified nucleosides include, but are not limited to, 2'-OCH3, 2'-methoxyethoxy (2'-O—CH$_2$CH$_2$OCH$_3$, Martin et al., Hely. Chim. Acta, 1995, 78, 486-504), a bicyclic sugar modified nucleoside, 2'-dimethylaminooxyethoxy (O(CH2) 2ON(CH3)2, 2'-dimethylaminoethoxyethoxy (2'-O—CH2-O—CH2-N(CH3)2), methoxy (—O—CH3), aminopropoxy (—OCH$_2$CH$_2$CH$_2$NH$_2$), allyl (—CH$_2$—CH=CH$_2$), —O-allyl (—O—CH$_2$—CH=CH$_2$) and 2'-acetamido (2'-O—CH$_2$C(=O)NR1R1 wherein each R1 is independently, H or C1-C1 alkyl.

Representative U.S. patents that teach the preparation of such 2'-modified nucleosides include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with this application, and each of which is herein incorporated by reference.

In one aspect the present invention provides oligomeric compounds having at least one stability enhancing internucleoside linkage. The term "stability enhancing internucleoside linkage" or "stabilizing internucleoside linking group" is meant to include all manner of internucleoside linkages that provide enhanced nuclease stability to oligomeric compounds relative to that provided by phosphodiester internucleoside linkages. Thus, stability enhancing internucleoside linkages are linkages other than phosphodiester internucleoside linkages. An example of such stability enhancing internucleoside linkages includes, but is not limited to, phosphorothioates internucleoside linkages.

Representative U.S. patents that teach the preparation of stability enhancing internucleoside linkages include, but are not limited to, U.S. Pat. Nos. 3,687,808; 5,286,717; 5,587, 361; 5,672,697; 5,489,677; 5,663,312; 5,646,269 and 5,677, 439, each of which is herein incorporated by reference.

Oligomeric Compounds

In certain embodiments, the present invention provides oligomeric compounds. In certain such embodiments, oligomeric compounds have antisense activity. In certain such embodiments, oligomeric compounds have splice altering activity. In certain embodiments, oligomeric compounds alter poly-adenylation. In certain embodiments, oligomeric compounds interfere with translation. In certain embodiments, oligomeric compounds have RNase H independent antisense activity.

In certain embodiments, the present invention provides oligomeric compounds comprising modifications. In certain embodiments the present invention provides oligomeric compounds comprising motifs of modifications. In certain embodiments, modifications and motifs suitable for the present invention may be found in WO 2007/090073, which is hereby incorporated by reference in its entirety for any purpose.

Oligomeric Compound Modifications

As is known in the art, a nucleoside is a base-sugar combination. The base (or nucleobase) portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal nucleobase complementarity and may therefore fold in a manner as to produce a fully or partially double-stranded structure. Within the unmodified oligonucleotide structure, the phosphate groups are commonly referred to as forming the internucleoside linkages of the oligonucleotide. The unmodified internucleoside linkage of RNA and DNA is a 3' to 5' phosphodiester linkage.

Modified Internucleoside Linking Groups

Specific examples of oligomeric compounds include oligonucleotides containing modified, i.e. non-naturally occurring internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases.

Oligomeric compounds of the invention can have one or more modified internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

One suitable phosphorus-containing modified internucleoside linkage is the phosphorothioate internucleoside linkage. A number of other modified oligonucleotide backbones (internucleoside linkages) are known in the art and may be useful in the context of this invention.

Representative U.S. patents that teach the preparation of phosphorus-containing internucleoside linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 5,625,050, 5,489,677, and 5,602,240 each of which is herein incorporated by reference.

Modified oligonucleoside backbones (internucleoside linkages) that do not include a phosphorus atom therein have internucleoside linkages that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having amide backbones; and others, including those having mixed N, O, S and CH2 component parts.

Representative U.S. patents that teach the preparation of the above non-phosphorous-containing oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Oligomeric compounds can also include oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring with for example a morpholino ring, is also referred to in the art as being a sugar surrogate. The heterocyclic base moiety or a modified heterocyclic base moiety is maintained for hybridization with an appropriate target nucleic acid. Oligonucleotide mimetics can include oligomeric compounds such as peptide nucleic acids (PNA) and cyclohexenyl nucleic acids (known as CeNA, see Wang et al., J. Am. Chem. Soc., 2000, 122, 8595-8602) Representative U.S. patents that teach the preparation of oligonucleotide mimetics include, but are not limited to, U.S. Pat. Nos. 5,539,082; 5,714,331; and 5,719,262, each of which is herein incorporated by reference. Another class of oligonucleotide mimetic is referred to as phosphonomonoester nucleic acid and incorporates a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology. Another oligonucleotide mimetic has been reported wherein the furanosyl ring has been replaced by a cyclobutyl moiety.

Modified Sugar Moieties

Oligomeric compounds of the invention can also contain one or more modified or substituted sugar moieties. The base moieties are maintained for hybridization with an appropriate nucleic acid target compound. Sugar modifications can impart nuclease stability, binding affinity or some other beneficial biological property to the oligomeric compounds. Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. A large number of sugar modifications are known in the art, sugars modified at the 2' position and those which have a bridge between any 2 atoms of the sugar (such that the sugar is bicyclic) are particularly useful in this invention. Examples of sugar modifications useful in this invention include, but are not limited to compounds comprising a sugar substituent group selected from: OH; F; O-, S-, or N-alkyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are: 2-methoxyethoxy (also known as 2'-O-methoxyethyl, 2'-MOE, or 2'-OCH$_2$CH$_2$OCH$_3$), 2'-O-methyl (2'-β-CH$_3$), 2'-fluoro (2'-F); or bicyclic sugar modified nucleosides having a bridging group connecting the 4' carbon atom to the 2' carbon atom wherein example bridge groups include —CH$_2$—O—, —(CH$_2$)$_2$—O— or —CH$_2$—N(R$_3$)—O— wherein R$_3$ is H or $C_1$-$C_{12}$ alkyl.

In one embodiment, oligomeric compounds include one or more nucleosides having a substituent group at the 2'-position. Examples of 2'-sugar substituent groups useful in this invention include, but are not limited to: OH; F; O—, S—, or N-alkyl; O—, S—, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[(CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(=O)N(H)CH$_3$ and O(CH$_2$)$_n$ON[(CH$_2$)$_n$CH$_3$]$_2$, where n and m are from 1 to about 10. Other 2'-sugar substituent groups include: $C_1$ to $C_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an oligomeric compound, and other substituents having similar properties.

One modification that imparts increased nuclease resitance and a very high binding affinity to nucleotides is the 2'-MOE side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

2'-Sugar substituent groups may be in the arabino (up) position or ribo (down) position. One 2'-arabino modification is 2'-F. Similar modifications can also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Representative sugar substituents groups are disclosed in U.S. Pat. No. 6,172,209 entitled "Capped 2'-Oxyethoxy Oligonucleotides," hereby incorporated by reference in its entirety.

Representative cyclic sugar substituent groups are disclosed in U.S. Pat. No. 6,271,358 entitled "RNA Targeted 2'-Oligomeric compounds that are Conformationally Preorganized," hereby incorporated by reference in its entirety.

Representative guanidino substituent groups are disclosed in U.S. Pat. No. 6,593,466 entitled "Functionalized Oligomers," hereby incorporated by reference in its entirety.

Representative acetamido substituent groups are disclosed in U.S. Pat. No. 6,147,200 which is hereby incorporated by reference in its entirety.

Another group of modifications includes nucleosides having sugar moieties that are bicyclic thereby locking the sugar conformational geometry. Such modifications may impart nuclease stability, binding affinity or some other beneficial biological property to the oligomeric compounds. The most studied of these nucleosides is a bicyclic sugar modified nucleoside having a 4'-CH$_2$—O-2' bridge. This bridge attaches under the sugar as shown forcing the sugar ring into a locked 3'-endo conformation geometry. The alpha-L nucleoside has also been reported wherein the linkage is above the ring and the heterocyclic base is in the alpha rather than the beta-conformation (see U.S. Patent Application Publication No.: Application 2003/0087230). The xylo analog has also been prepared (see U.S. Patent Application Publication No.: 2003/0082807). Another bicyclic sugar modified nucleoside having similar properties to the 4'-CH$_2$—O-2' bridged nucleoside has one added methylene group in the bridge 4'-(CH$_2$)$_2$—O-2' (Kaneko et al., U.S. Patent Application Publication No.: US 2002/0147332, Singh et al., Chem. Commun., 1998, 4, 455-456, also see U.S. Pat. Nos. 6,268,490 and 6,670,461 and U.S. Patent Application Publication No.: US 2003/0207841). Oligomeric compounds incorporating these bicyclic sugar modified nucleosides (4'-(CH$_2$)$_{1(or)}$—O-2') display very high duplex thermal stabilities with complementary DNA and RNA (Tm=+3 to +10 C), stability towards 3'-exonucleolytic degradation and good solubility properties.

The synthesis and preparation of the bicyclic sugar modified monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630; WO 98/39352 and WO 99/14226).

Other bicyclic sugar modified nucleoside analogs such as the 4'-CH$_2$—S-2' analog have also been prepared (Kumar et al., Bioorg. Med. Chem. Lett., 1998, 8, 2219-2222). Preparation of other bicyclic sugar analogs containing oligodeoxyribonucleotide duplexes as substrates for nucleic acid polymerases has also been described (Wengel et al., PCT International Application WO 98-DK393 19980914).

Nucleobase Modifications

Oligomeric compounds of the invention can also contain one or more nucleobase (often referred to in the art simply as "base") modifications or substitutions which are structurally distinguishable from, yet functionally interchangeable with, naturally occurring or synthetic unmodified nucleobases. Such nucleobase modifications can impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases, many examples of which such as 5-methylcytosine (5-me-C), 5-hydroxymethyl cytosine, 7-deazaguanine and 7-deazaadenine among others.

Heterocyclic base moieties can also include those in which the purine or pyrimidine base is replaced with other heterocycles, for example 7-deaza-adenine, 7-deazaguanosine, 2-aminopyridine and 2-pyridone. Some nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2 aminopropyladenine, 5-propynyluracil and 5-propynylcytosine.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs.

Representative cytosine analogs that make 3 hydrogen bonds with a guanosine in a second strand include 1,3-diazaphenoxazine-2-one (R$_{10}$=O, R$_{11}$-R$_{14}$=H) (Kurchavov, et al., Nucleosides and Nucleotides, 1997, 16, 1837-1846), 1,3-diazaphenothiazine-2-one (R$_{10}$=S, R$_{11}$-R$_{14}$=H), (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (R$_{10}$=O, R$_{11}$-R$_{14}$=F) (Wang, J.; Lin, K.-Y., Matteucci, M. Tetrahedron Lett. 1998, 39, 8385-8388). When incorporated into oligonucleotides, these base modifications were shown to hybridize with complementary guanine and the latter was also shown to hybridize with adenine and to enhance helical thermal stability by extended stacking interactions (also see U.S. Patent Application Publication 20030207804 and U.S. Patent Application Publication 20030175906, both of which are incorporated herein by reference in their entirety).

Helix-stabilizing properties have been observed when a cytosine analog/substitute has an aminoethoxy moiety attached to the rigid 1,3-diazaphenoxazine-2-one scaffold (R$_{10}$=O, R$_{11}$=O—(CH$_2$)$_2$—NH$_2$, R$_{12-14}$=H) (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Tricyclic heterocyclic compounds and methods of using them that are amenable to the present invention are disclosed in U.S. Pat. No. 6,028,183, and U.S. Pat. No. 6,007,992, the contents of both are incorporated herein in their entirety.

The enhanced binding affinity of the phenoxazine derivatives together with their sequence specificity makes them valuable nucleobase analogs for the development of more potent antisense-based drugs. The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. Patent Application Publication 20030158403, each of which is incorporated herein by reference in its entirety.

Certain nucleobase substitutions, including 5-methylcytosine substitutions, are particularly useful for increasing the binding affinity of the oligonucleotides of the invention. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Conjugated Oligomeric Compounds

One substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, carbohydrates, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomeric compound uptake, enhance oligomeric compound resistance to degradation, and/or strengthen hybridization with RNA. Groups that enhance the pharmacokinetic properties, in the context of this invention, include groups that improve oligomeric compound uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety and a variety of others known in the art.

Furthermore, the oligomeric compounds of the invention can have one or more moieties bound or conjugated, which facilitates the active or passive transport, localization, or compartmentalization of the oligomeric compound. Cellular localization includes, but is not limited to, localization to within the nucleus, the nucleolus, or the cytoplasm. Compartmentalization includes, but is not limited to, any directed movement of the oligonucleotides of the invention to a cellular compartment including the nucleus, nucleolus, mitochondrion, or imbedding into a cellular membrane.

Furthermore, the oligomeric compounds of the invention comprise one or more conjugate moieties which facilitate posttranscriptional modification.

Certain conjugate groups amenable to the present invention include lipid moieties such as a cholesterol moiety (Letsinger et al., Proc. Natl. Acad. Sci. USA, 1989, 86, 6553); cholic acid (Manoharan et al., Bioorg. Med. Chem. Lett., 1994, 4, 1053); a thioether, e.g., hexyl-5-tritylthiol (Manoharan et al., Ann. N.Y. Acad. Sci., 1992, 660, 306; Manoharan et al., Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49); a phospholipid, e.g., dihexadecyl-rac-glycerol or triethylammonium-1,2-di-O-hexadecyl-rac-glycero-3-H-phosphonate (Manoharan et al., Tetrahedron Lett., 1995, 36, 3651; Shea et al., Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al., Biochim. Biophys. Acta, 1995, 1264, 229); or an octadecylamine or hexylamino-carbonyl-oxycholesterol moiety (Crooke et al., J. Pharmacol. Exp. Ther., 1996, 277, 923).

Conjugate groups can be attached to various positions of an oligomeric compound directly or via an optional linking group. The term linking group is intended to include all groups amenable to attachment of a conjugate group to an oligomeric compound. Linking groups are bivalent groups useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the linker comprises a chain structure or an oligomeric compound of repeating units such as ethylene glyol or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted C1-C10 alkyl, substituted or unsubstituted C2-C10 alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl. Further representative linking groups are disclosed for example in WO 94/01550 and WO 94/01550.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications can protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. For double-stranded oligomeric compounds, the cap may be present at either or both termini of either strand. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5',-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Oligomeric Compound Chemical Motifs

Oligomeric compounds can have chemically modified subunits arranged in specific orientations along their length. A "chemical motif" is defined as the arrangement of chemical modifications throughout an oligomeric compound In certain embodiments, oligomeric compounds of the invention are uniformly modified. As used herein, in a "uniformly modified" oligomeric compound a chemical modification of a sugar, base, internucleoside linkage, or combination thereof, is applied to each subunit of the oligomeric compound. In one embodiment, each sugar moiety of a uniformly modified oligomeric compound is modified. In other embodiments, each internucleoside linkage of a uniformly modified oligomeric compound is modified. In further embodiments, each sugar and each internucleoside linkage of uniformly modified oligomeric compounds bears a modification. Examples of uniformly modified oligomeric compounds include, but are not limited to, uniform 2'-MOE sugar moieties; uniform 2'-MOE and uniform phosphorothioate backbone; uniform 2'-OMe; uniform 2'-OMe and uniform phosphorothioate backbone; uniform 2'-F; uniform 2'-F and uniform phosphorothioate backbone; uniform phosphorothioate backbone; uniform deoxynucleotides; uniform ribonucleotides; uniform phosphorothioate backbone; and combinations thereof.

As used herein the term "positionally modified motif" is meant to include a sequence of uniformly sugar modified nucleosides wherein the sequence is interrupted by two or more regions comprising from 1 to about 8 sugar modified nucleosides wherein internal regions are generally from 1 to about 6 or from 1 to about 4. The positionally modified motif includes internal regions of sugar modified nucleoside and can also include one or both termini. Each particular sugar modification within a region of sugar modified nucleosides essentially uniform. The nucleotides of regions are distinguished by differing sugar modifications. Positionally modified motifs are not determined by the nucleobase sequence or the location or types of internucleoside linkages. The term positionally modified oligomeric compound includes many different specific substitution patterns. A number of these substitution patterns have been prepared and tested in compositions. In one embodiment the positionally modified oligomeric compounds may comprise phosphodiester internucleotide linkages, phosphorothioate internucleotide linkages, or a combination of phosphodiester and phosphorothioate internucleotide linkages.

In some embodiments, positionally modified oligomeric compounds include oligomeric compounds having clusters of a first modification interspersed with a second modification, as follows 5'-MMmmMmMMMmmmmMMMMmm-mmm-3'; and 5'-MMmMMmMMmMMmMMmMMmMM-mMM-3'; wherein "M" represent the first modification, and "m" represents the second modification. In one embodiment, "M" is 2'-MOE and "m" is a bicyclic sugar modified nucleoside having a 4'-$(CH_2)_n$—O-2' where n is 1 or 2. In other embodiments, "M" is 2'-MOE and "m" is 2'-F. In other embodiments, "M" is 2'-OMe and "m" is 2'-F.

In some embodiments, oligomeric compounds are chimeric oligomeric compounds.

In certain embodiments, chimeric oligomeric compounds are gapmers. The types of sugar moieties that are used to differentiate the regions of a gapmer oligomeric compound include β-D-ribonucleosides, β-D-deoxyribonucleosides, or 2'-modified nucleosides disclosed herein, including, without limitation, 2'-MOE, 2'-fluoro, 2'-O—$CH_3$, and bicyclic sugar modified nucleosides. In one embodiment, each region is uniformly modified. In another embodiment, the nucleosides of the internal region uniform sugar moieties that are different than the sugar moieties in an external region. In one non-limiting example, the gap is uniformly comprised of a first 2'-modified nucleoside and each of the wings is uniformly comprised of a second 2'-modified nucleoside.

Gapmer oligomeric compounds are further defined as being either "symmetric" or "asymmetric". A gapmer having the same uniform sugar modification in each of the wings is termed a "symmetric gapmer oligomeric compound." A gapmer having different uniform modifications in each wing is termed an "asymmetric gapmer oligomeric compound." In one embodiment, gapmer oligomeric compounds such as these can have, for example, both wings comprising 2'-MOE modified nucleosides (symmetric gapmer) and a gap comprising β-D-ribonucleosides or β-D-deoxyribonucleosides. In another embodiment, a symmetric gapmer can have both wings comprising 2'-MOE modified nucleosides and a gap comprising 2'-modified nucleosides other than 2'-MOE modified nucleosides. Asymmetric gapmer oligomeric compounds, for example, can have one wing comprising 2'-OCH$_3$ modified nucleosides and the other wing comprising 2'-MOE modified nucleosides with the internal region (gap) comprising β-D-ribonucleosides, β-D-deoxyribonucleosides, β-D-modified nucleosides that are other than 2'-MOE or 2'-OCH3 modified nucleosides. These gapmer oligomeric compounds may comprise phosphodiester internucleotide linkages, phosphorothioate internucleotide linkages, or a combination of phosphodiester and phosphorothioate internucleotide linkages.

In some embodiments, each wing of a gapmer oligomeric compounds comprises the same number of subunits. In other embodiments, one wing of a gapmer oligomeric compound comprises a different number of subunits than the other wing of a gapmer oligomeric compound. In one embodiment, the wings of gapmer oligomeric compounds have, independently, from 1 to about 3 nucleosides. Suitable wings comprise from 2 to about 3 nucleosides. In one embodiment, the wings can comprise 2 nucleosides. In another embodiment, the 5'-wing can comprise 1 or 2 nucleosides and the 3'-wing can comprise 2 or 3 nucleosides. The present invention therefore includes gapped oligomeric compounds wherein each wing independently comprises 1, 2 or 3 sugar modified nucleosides. In one embodiment, the internal or gap region comprises from 15 to 23 nucleosides, which is understood to include 15, 16, 17, 18, 19, 20, 21, 22 and 23 nucleotides. In a further embodiment, the internal or gap region is understood to comprise from 17 to 21 nucleosides, which is understood to include 17, 18, 19, 20, or 21 nucleosides. In another embodiment, the internal or gap region is understood to comprise from 18 to 20 nucleosides, which is understood to include 18, 19 or 20 nucleosides. In one preferred embodiment, the gap region comprises 19 nucleosides. In one embodiment, the oligomeric compound is a gapmer oligonucleotides with full length complementarity to its target miRNA. In a further embodiment, the wings are 2'-MOE modified nucleosides and the gap comprises 2'-fluoro modified nucleosides. In one embodiment one wing is 2 nucleosides in length and the other wing is 3 nucleosides in length. In an additional embodiment, the wings are each 2 nucleosides in length and the gap region is 19 nucleotides in length.

Examples of chimeric oligomeric compounds include, but are not limited to, a 23 nucleobase oligomeric compound having a central region comprised of a first modification and wing regions comprised of a second modification (5'MMmmmmmmmmmmmmmmmmmmmmMM3'); a 22 nucleobase compound having a central region comprised of a first modification and wing regions comprised of a second modification (5'MMmmmmmmmmmmmmmmmmmmmMM3'); and a 21 nucleobase compound having a central region comprised of a first modification and wing regions comprised of a second modification (5'MMmmmmmmmmmmmmmmmmmMM3'); wherein "M" represents the first modification and "m" represents the second modification. In one non-limiting example, "M" may be 2'-O-methoxyethyl and "m" may be 2'-fluoro.

In one embodiment, chimeric oligomeric compounds are "hemimer oligomeric compounds" wherein chemical modifications to sugar moieties and/or internucleoside linkage distinguish a region of subunits at the 5' terminus from a region of subunits at the 3' terminus of the oligomeric compound.

Chimeric oligomeric compounds typically contain at least one region modified so as to confer increased resistance to nuclease degradation, increased cellular uptake, and/or increased binding affinity for the target nucleic acid. An additional region of the oligomeric compound can, for example, contain a different modification, and in some cases may serve as a substrate for enzymes capable of cleaving RNA:DNA or RNA:RNA hybrids. By way of example, an oligomeric compound can be designed to comprise a region that serves as a substrate for RNase H. RNase H is a cellular endonuclease which cleaves the RNA strand of an RNA:DNA duplex. Activation of RNase H by an oligomeric compound having a cleavage region, therefore, results in cleavage of the RNA target, thereby enhancing the efficiency of the oligomeric compound. Alternatively, the binding affinity of the oligomeric compound for its target nucleic acid can be varied along the length of the oligomeric compound by including regions of chemically modified nucleosides which have exhibit either increased or decreased affinity as compared to the other regions. Consequently, comparable results can often be obtained with shorter oligomeric compounds having substrate regions when chimeras are used, compared to for example phosphorothioate deoxyoligonucleotides hybridizing to the same target region.

Chimeric oligomeric compounds of the invention can be formed as composite structures of two or more oligonucleotides, oligonucleotide mimics, oligonucleotide analogs, oligonucleosides and/or oligonucleoside mimetics as described above. Such oligomeric compounds have also been referred to in the art as hybrids, hemimers, gapmers or inverted gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

In another aspect of the chimeric oligomeric compound there is a "gap-disabled" motif (also referred to as "gap-ablated motif"). In the gap-disabled motif, the internal region is interrupted by a chemical modification distinct from that of the internal region. The wing regions can be uniformly sized or differentially sized as also described above. Examples of gap-disabled motifs are as follows: 5'MMMMMmmmMMMmmmmMMMM3'; 5'MMMM-mmmmmmMmmmmmmmmMM3'; 5'MMmmmmmmmmm-mMMMmmmMM3'; wherein "m" represents one sugar modification and "M" represents a different sugar modification As used in the present invention the term "alternating motif" is meant to include a contiguous sequence of nucleosides comprising two different nucleosides that alternate for essentially the entire sequence of the oligomeric compound. The pattern of alternation can be described by the formula: 5'-A(-L-B-L-A)n(-L-B)nn-3' where A and B are nucleosides differentiated by having at least different sugar groups, each L is an internucleoside linking group, nn is 0 or 1 and n is from about 7 to about 11. This permits alternating oligomeric compounds from about 17 to about 24 nucleosides in length. This length range is not meant to be limiting as longer and shorter oligomeric compounds are also amenable to the present invention. This formula also allows for even and odd lengths for alternating oligomeric compounds wherein the 3' and 5'-terminal nucleosides are the same (odd) or different (even). These alternating oligomeric compounds may comprise phosphodiester internucleotide linkages, phosphorothioate internucleotide linkages, or a combination of phosphodiester and phosphorothioate internucleotide linkages.

The "A" and "B" nucleosides comprising alternating oligomeric compounds of the present invention are differentiated from each other by having at least different sugar moieties. Each of the A and B nucleosides has a modified sugar moiety selected from β-D-ribonucleosides, β-D-deoxyribonucleosides, 2'-modified nucleosides (such 2'-modified nucleosides may include 2'-MOE, 2'-fluoro, and 2'-O—CH$_3$, among others), and bicyclic sugar modified nucleosides. The alternating motif is independent from the nucleobase sequence and the internucleoside linkages. The internucleoside linkage can vary at each position or at particular selected positions or can be uniform or alternating throughout the oligomeric compound.

As used in the present invention the term "fully modified motif" is meant to include a contiguous sequence of sugar modified nucleosides wherein essentially each nucleoside is modified to have the same modified sugar moiety. Suitable sugar modified nucleosides for fully modified strands of the invention include, but are not limited to, 2'-Fluoro (2'F), 2'-O(CH$_2$)$_2$OCH$_3$ (2'-MOE), 2'-OCH$_3$ (2'-β-methyl), and bicyclic sugar modified nucleosides. In one aspect the 3' and 5'-terminal nucleosides are left unmodified. In a preferred embodiment, the modified nucleosides are either 2'-MOE, 2'-F, 2'-O-Me or a bicyclic sugar modified nucleoside.

As used in the present invention the term "hemimer motif" is meant to include a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified oligomeric compound. An example of a typical hemimer is an oligomeric compound comprising β-D-ribonucleosides or β-D-deoxyribonucleosides that have a sequence of sugar modified nucleosides at one of the termini. One hemimer motif includes a sequence of β-D-ribonucleosides or β-D-deoxyribonucleosides having from 2-12 sugar modified nucleosides located at one of the termini. Another hemimer motif includes a sequence of β-D-ribonucleosides or β-D-deoxyribonucleosides having from 2-6 sugar modified nucleosides located at one of the termini with from 2-4 being suitable. In a preferred embodiment of the invention, the oligomeric compound comprises a region of 2'-MOE modified nculeotides and a region of β-D-deoxyribonucleosides. In one embodiment, the β-D-deoxyribonucleosides comprise less than 13 contiguous nucleotides within the oligomeric compound. These hemimer oligomeric compounds may comprise phosphodiester internucleotide linkages, phosphorothioate internucleotide linkages, or a combination of phosphodiester and phosphorothioate internucleotide linkages.

As used in the present invention the term "blockmer motif" is meant to include a sequence of nucleosides that have uniform sugars (identical sugars, modified or unmodified) that is internally interrupted by a block of sugar modified nucleosides that are uniformly modified and wherein the modification is different from the other nucleosides. More generally, oligomeric compounds having a blockmer motif comprise a sequence of β-D-ribonucleosides or β-D-deoxyribonucleosides having one internal block of from 2 to 6, or from 2 to 4 sugar modified nucleosides. The internal block region can be at any position within the oligomeric compound as long as it is not at one of the termini which would then make it a hemimer. The base sequence and internucleoside linkages can vary at any position within a blockmer motif.

Nucleotides, both native and modified, have a certain conformational geometry which affects their hybridization and affinity properties. The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as, but not limited to, antisense mechanisms, including RNase H-mediated and RNA interference mechanisms, as these mechanisms involved the hybridization of a synthetic sequence strand to an RNA target strand. In the case of RNase H, effective inhibition of the mRNA requires that the antisense sequence achieve at least a threshold of hybridization.

One routinely used method of modifying the sugar puckering is the substitution of the sugar at the 2'-position with a substituent group that influences the sugar geometry. The influence on ring conformation is dependent on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is also correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-Olcuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry. Properties that are enhanced by using more stable 3'-endo nucleosides include but are not limited to modulation of pharmacokinetic properties through modification of protein binding, protein off-rate, absorption and clearance; modulation of nuclease stability as well as chemical stability; modulation of the binding affinity and specificity of the oligomeric compound (affinity and specificity for enzymes as well as for complementary sequences); and increasing efficacy of RNA cleavage.

The conformation of modified nucleosides and their oligomers can be estimated by various methods such as molecular dynamics calculations, nuclear magnetic resonance spectroscopy and CD measurements. Hence, modifications predicted to induce RNA-like conformations (A-form duplex geometry in an oligomeric context), are useful in the oligomeric compounds of the present invention. The synthesis of modified nucleosides amenable to the present invention are known in the art (see for example, Chemistry of Nucleosides and Nucleotides Vol 1-3, ed. Leroy B. Townsend, 1988, Plenum Press.)

In one aspect, the present invention is directed to oligomeric compounds that are designed to have enhanced properties compared to native RNA or DNA. One method to design optimized or enhanced oligomeric compounds involves each nucleoside of the selected sequence being scrutinized for possible enhancing modifications. One modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention may include at least one 5'-modified phosphate group on a single strand or on at least one 5'-position of a double-stranded sequence or sequences. Other modifications considered are internucleoside linkages, conjugate groups, substitute sugars or bases, substitution of one or more nucleosides with nucleoside mimetics and any other modification that can enhance the desired property of the oligomeric compound.

In certain embodiments, the present invention provides oligomeric compounds, including antisense oligomeric compounds and antidote oligomeric compounds, of any of a variety of ranges of lengths. In certain embodiments, the invention provides oligomeric compounds consisting of X-Y linked oligonucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked nucleosides.

In certain embodiments, the invention provides a method of modulating expression of a target protein in a cell comprising contacting the cell with an oligomeric compound comprising a contiguous sequence of nucleosides having the formula I:

$$T_1\text{-}(Nu_1)_{n1}\text{-}(Nu_2)_{n2}\text{-}(Nu_3)_{n3}\text{-}(Nu_4)_{n4}\text{-}(Nu_5)_{n5}\text{-}T_2,$$

wherein:

$Nu_1$ and $Nu_5$ are, independently, 2' stabilizing nucleosides;
$Nu_2$ and $Nu_4$ are β-D-2'-deoxy-2'-fluororibofuranosyl nucleosides;
$Nu_3$ is a 2'-modified nucleoside;
each of n1 and n5 is, independently, from 0 to 3;
the sum of n2 plus n4 is between 10 and 25;
n3 is from 0 and 5; and
each $T_1$ and $T_2$ is, independently, H, a hydroxylprotecting group, an optionally linked conjugate group or a capping group; and thereby modulating expression of the target protein. In certain such embodiments, the sum of n2 and n4 is 13 or 14; n1 is 2; n3 is 2 or 3; and n5 is 2. In certain such embodiments, formula I is selected from Table A.

TABLE A

| n1 | n2 | n3 | n4 | n5 |
|----|----|----|----|----|
| 2 | 16 | 0 | 0 | 2 |
| 2 | 2 | 3 | 11 | 2 |
| 2 | 5 | 3 | 8 | 2 |
| 2 | 8 | 3 | 5 | 2 |
| 2 | 11 | 3 | 2 | 2 |
| 2 | 9 | 3 | 4 | 2 |
| 2 | 10 | 3 | 3 | 2 |
| 2 | 3 | 3 | 10 | 2 |
| 2 | 4 | 3 | 9 | 2 |
| 2 | 6 | 3 | 7 | 2 |
| 2 | 7 | 3 | 6 | 2 |
| 2 | 8 | 6 | 2 | 2 |
| 2 | 2 | 2 | 12 | 2 |
| 2 | 3 | 2 | 11 | 2 |
| 2 | 4 | 2 | 10 | 2 |
| 2 | 5 | 2 | 9 | 2 |
| 2 | 6 | 2 | 8 | 2 |
| 2 | 7 | 2 | 7 | 2 |
| 2 | 8 | 2 | 6 | 2 |
| 2 | 9 | 2 | 5 | 2 |
| 2 | 10 | 2 | 4 | 2 |
| 2 | 11 | 2 | 3 | 2 |
| 2 | 12 | 2 | 2 | 2 |

Table A is intended to illustrate, but not to limit the present invention. The oligomeric compounds depicted in Table A each comprise 20 nucleosides. Oligomeric compounds comprising more or fewer nucleosides can easily by designed by selecting different numbers of nucleosides for one or more of n1-n5.

Certain Targets and Mechanisms

In certain embodiments, oligomeric compounds provided herein are targeted to a pre-mRNA. In certain embodiments, such oligomeric compounds alter splicing of the pre-mRNA. In certain such embodiments, the ratio of one variant of a target mRNA to another variant of the target mRNA is altered. In certain such embodiments, the ratio of one variant of a target protein to another variant of the target protein is altered. Certain oligomeric compounds and nucleobase sequences that may be used to alter splicing of a pre-mRNA may be found for example in U.S. Pat. No. 6,210,892; U.S. Pat. No. 5,627,274; U.S. Pat. No. 5,665,593; 5,916,808; U.S. Pat. No. 5,976,879; US2006/0172962; US2007/002390; US2005/0074801; US2007/0105807; US2005/0054836; WO 2007/090073; WO2007/047913, Hua et al., PLoS Biol 5(4):e73; Vickers et al., J. Immunol 2006 Mar. 15; 176(6): 3652-61, each of which is hereby incorporated by reference in its entirety for any purpose. In certain embodiments antisense sequences that alter splicing are modified according to motifs of the present invention. In certain embodiments, oligomeric compounds of the present invention redirect polyadenylation of pre-mRNA. See, for example Vickers et al., Nucleic Acids Res. 29(6):1293-1299, which is hereby incorporated by reference in its entirety for any purpose. In certain embodiments antisense sequences that redirect polyadenylation are modified according to motifs of the present invention.

In certain embodiments, the invention provides oligomeric compounds complementary to a pre-mRNA encoding Bcl-x. In certain such embodiments, the oligomeric compound alters splicing of Bcl-x. Certain sequences and regions useful for altering splicing of Bcl-x may be found in U.S. Pat. No. 6,172,216; U.S. Pat. No. 6,214,986; U.S. Pat. No. 6,210,892; US2007/002390 and WO 2007/028065, each of which is hereby incorporated by reference in its entirety for any purpose.

In certain embodiments, the present invention provides compounds complementary to a pre-mRNA encoding MyD88. In certain such embodiments, the oligomeric compound alters splicing of MyD88. Certain sequences and regions useful for altering splicing of MyD88 may be found in U.S. application Ser. No. 11/336,785, which is hereby incorporated by reference in its entirety for any purpose.

In certain embodiments, the present invention provides compounds complementary to a pre-mRNA encoding Lamin A (LMN-A). In certain such embodiments, the oligomeric compound alters splicing of Lamin A Certain sequences and regions useful for altering splicing of Lamin A may be found in PCT/US2006/041018, which is hereby incorporated by reference in its entirety for any purpose.

In certain embodiments, the present invention provides compounds complementary to a pre-mRNA encoding SMN2. In certain such embodiments, the oligomeric compound alters splicing of SMN2. Certain sequences and regions useful for altering splicing of SMN2 may be found in PCT/US06/024469, which is hereby incorporated by reference in its entirety for any purpose.

In certain embodiments, the present invention provides compounds complementary to a pre-mRNA encoding TNF superfamily of receptors. In certain such embodiments, the oligomeric compound alters splicing of TF. Certain sequences and regions useful for altering splicing of TNF may be found in US2007/0105807, which is hereby incorporated by reference in its entirety for any purpose.

Synthesis, Purification and Analysis

Oligomerization of modified and unmodified nucleosides and nucleotides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds provided herein can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Methods of purification and analysis of oligomeric compounds are known to those skilled in the art. Analysis methods include capillary electrophoresis (CE) and electrospray-mass spectroscopy. Such synthesis and analysis methods can be performed in multi-well plates. The method of the invention is not limited by the method of oligomeric compound purification.

Compositions and Methods for Formulating Pharmaceutical Compositions

Oligomeric compounds may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Oligomeric compounds, including antisense compounds and/or antidote compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound and/or antidote compound and a pharmaceutically acceptable diluent. In certain embodiments, the pharmaceutically acceptable diluent is PBS.

Pharmaceutical compositions comprising oligomeric compounds encompass any pharmaceutically acceptable salts, esters, or salts of such esters. In certain embodiments, pharmaceutical compositions comprising oligomeric compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active oligomeric compound.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

The nucleoside sequences set forth in the sequence listing and Examples, are independent of any modification to a sugar moiety, a monomeric linkage, or a nucleobase. As such, oligomeric compounds defined by a SEQ ID NO may comprise, independently, one or more modifications to a sugar moiety, an internucleoside linkage, or a nucleobase. Oligomeric compounds described by Isis Number (Isis NO.) indicate a combination of nucleobase sequence and one or more modifications to a sugar moiety, an internucleoside linkage, or a nucleobase, as indicated.

EXAMPLES

Example 1

EGFP-654 Transgenic Mouse Model

EGFP-654 transgenic mice transcribe the EGFP-654 transgene throughout the body. In this mouse model, the transgene encoding enhanced green fluorescent protein (EGFP) is interrupted by an aberrantly spliced mutated intron 2 of the human β-globin gene. The mutation at nucleotide 654 of intron 2 of human β-globin activates aberrant splice sites and leads to retention of the intron fragment in spliced mRNA, preventing proper translation of EGFP. Aberrant splicing of this intron prevents expression of EGFP-654 in all tissues. Blocking the aberrant splice site restores normal pre-mRNA splicing and EGFP expression. Thus, EGFP-654 transgenic mice can be used to evaluate oligomeric compounds designed to modulate splicing. Generation of EGFP-654 transgenic mice and control EGFP-WT mice is described in Sazani et al. (2002, *Nature Biotechnol.* 20:1228-1233). Briefly, plasmid CX-EGFP-654 was constructed from plasmid CXEGFP (Okabe et al. 1997, *FEBS Lett.* 407:313-319) as described by Sazani et al. (2001, *Nucleic Acids Res.* 29:3965-3974). To generate the CX-EGFP-WT plasmid, an EcoNI-Ppuml fragment of β-globin intron 2 from the CX-EGFG-654 plasmid was replaced by the same fragment from the intron 2 of the wild-type β-globin gene. Transgenic mice were produced using standard procedures by microinjection of the 3.8 kb PstI/SalI fragments of CX-EGFP-654 and CX-EGFP-WT into fertilized FVB/N mouse embryos.

Example 2

Design of Oligomeric Compounds for Modulation of Splicing

A series of oligomeric compounds was designed to modulate splicing of selected pre-mRNAs. The sequence and motif of each compound is shown in Table 1. Compounds were designed to target the 5' splice site of nucleotide 654 of the human β-globin intron 2 sequence of the EGFP-654 transgene. Underlined nucleosides are 2' MOE modified. Nucleosides that are not underlined are 2'-fluoro modified.

TABLE 1

Oligomeric compounds.

| ISIS # | | Sequence | Length | SEQ ID |
|---|---|---|---|---|
| 404029 | ('029) | TGCTATTACCTTAACCCAGA | 20 | 1 |
| 404030 | ('030) | TGCTATTACCTTAACCCAGA | 20 | 1 |
| 404031 | ('031) | GCTATTACCTTAACCCAG | 18 | 2 |
| 404032 | ('032) | GCTATTACCTTAACCCAG | 18 | 2 |

Underlined nucleosides comprise 2'MOE. Those not underlined comprise 2'-F.

Example 3

Modulation of EGFP-654 Pre-mRNA Splicing In Vivo

The EGFP-654 transgenic mouse system was used to evaluate oligomeric compounds for modulation of splicing. As described in Example 1, the EGFP-654 transgene contains the EGFP coding sequence interrupted by a mutated intron 2 of the human β-globin gene which contains an aberrant splice site. Due to aberrant splicing, EGFP is not expressed. Blockade of the aberrant splice site would allow EGFP expression in all tissues.

Twenty four EGFP-654 mice were each injected either with one of the oligomeric compounds form Table 1 at 25 mg/kg, with saline, or with 25 mg/kg of a control oligomeric compound having one or the other of the sequences of Table 1 and comprising LNA and DNA nucleosides. All antisense oligomeric compounds were dissolved in 0.9% saline at 2.5 mg/ml. 200 µL of oligonucleotide solution was used per injection. Injections were given daily, at approximately the same time each day. All mice were injected daily for 4 days and were sacrificed 24 hours after the last injection.

Tissue samples were flash frozen in liquid nitrogen and then homogenized in 800 µL of TRI-Reagent and samples were centrifuged for 1 min to remove cellular debris. The supernatant was transferred to a new tube and total RNA was isolated following the TRI-Reagent supplier's protocol. To test for a shift in the splicing pattern of EGFP-654 pre-mRNA, the RNA was analyzed by RT-PCR using primers that flank the alternatively spliced intron. $^{32}$P-ATP was included in the PCR reaction mixture. The PCR products were separated by electrophoresis on a 10% polyacrylamide gel and the gels were subjected to autoradiography. A correctly spliced EGFP-654 mRNA is smaller than the aberrantly spliced transcript and thus migrates faster in an electrophoretic gel. Quantitation of percent shift in splicing was determined using a TYPHOON phosphoimager and using IMAGEQUANT software. Results are provided in Table 2, below.

TABLE 2

Percent shift in splicing in various tissues of mice treated with oligomeric compounds targeting intron 2 of the human β-globin gene.

| Organ | Saline | Saline | LNA/DNA 20mer | LNA/DNA 18mer | '029 | '029 | '030 | '030 | '031 | '031 | '032 | '032 |
|---|---|---|---|---|---|---|---|---|---|---|---|---|
| Liver | 11 | 12 | 76 | 82 | 75 | 79 | 57 | 47 | 79 | 82 | 62 | 73 |
| Kidney | 2 | 1 | 21 | 23 | 9 | 10 | 10 | 8 | 13 | 15 | 13 | 13 |
| Lung | 1 | 2 | 9 | 7 | 6 | 9 | 6 | 5 | 10 | 11 | 13 | 12 |
| Small Inest. | 7 | ND | 72 | ND | 58 | 42 | 35 | 25 | ND | ND | ND | ND |
| Colon | 3 | ND | 63 | ND | 55 | 51 | 27 | 34 | ND | ND | ND | ND |
| Skel. Muscle | 0 | ND | 1 | ND | 3 | 3 | 2 | 0 | ND | ND | ND | ND |
| Spleen | 0 | ND | 31 | ND | 13 | 15 | 4 | 3 | ND | ND | ND | ND |
| Diaphragm | 0 | ND | 42 | ND | 44 | 44 | 45 | 17 | ND | ND | ND | ND |
| Heart | 1 | ND | 10 | ND | 6 | 5 | 6 | 4 | ND | ND | ND | ND |
| Stomach | 4 | ND | 17 | ND | 8 | 11 | 9 | 12 | ND | ND | ND | ND |
| Skin | 0 | ND | 19 | ND | 14 | 13 | 19 | 9 | ND | ND | ND | ND |
| Thymus | 3 | ND | 19 | ND | 15 | 13 | 12 | 9 | ND | ND | ND | ND |

The invention claimed is:

1. An oligomeric compound comprising a contiguous sequence of nucleosides having the formula I:

$$T_1\text{-}(Nu_1)_{n1}\text{-}(Nu_2)_{n2}\text{-}(Nu_3)_{n3}\text{-}(Nu_4)_{n4}\text{-}(Nu_5)_{n5}\text{-}T_2,$$

wherein:

$Nu_1$ and $Nu_5$ are, independently, 2' stabilizing nucleosides;

$Nu_2$ and $Nu_4$ are β-D-2'-deoxy-2'-fluororibofuranosyl nucleosides;

$Nu_3$ is a 2'-modified nucleoside;

each of n1 and n5 is, independently, from 0 to 3;

the sum of n2 plus n4 is between 10 and 25;

n3 is from 0 and 5; and each $T_1$ and $T_2$ is, independently, H, a hydroxyl protecting group, an optionally linked conjugate group or a capping group, wherein the sequence is complementary to a portion of a pre-mRNA encoding Bcl-x, MyD88, Lamin A, SMN2, or a TNF receptor.

2. The oligomeric compound of claim 1, wherein:
the sum of n2 and n4 is 16 or 17;
n1 is 2;
n3 is 2 or 3; and
n5 is 2.

3. The oligomeric compound of claim 1, wherein the formula I is selected from:
a) formula I: n1=2, n2=19, n3=0, n4=0, n5=2;
b) formula I: n1=2, n2=2, n3=3, n4=14, n5=2;
c) formula I: n1=2, n2=5, n3=3, n4=11, n5=2;
d) formula I: n1=2, n2=8, n3=3, n4=8, n5=2;
e) formula I: n1=2, n2=11, n3=3, n4=5, n5=2;
f) formula I: n1=2, n2=14, n3=3, n4=2, n5=2;
g) formula I: n1=2, n2=9, n3=3, n4=7, n5=2;
h) formula I: n1=2, n2=10, n3=3, n4=6, n5=2;
i) formula I: n1=2, n2=12, n3=3, n4=4, n5=2;
j) formula I: n1=2, n2=3, n3=3, n4=13, n5=2;
k) formula I: n1=2, n2=4, n3=3, n4=12, n5=2;
l) formula I: n1=2, n2=6, n3=3, n4=10, n5=2;
m) formula I: n1=2, n2=7, n3=3, n4=9, n5=2;
n) formula I: n1=2, n2=13, n3=3, n4=3, n5=2;
o) formula I: n1=2, n2=8, n3=6, n4=5, n5=2;
p) formula I: n1=2, n2=2, n3=2, n4=15, n5=2;
q) formula I: n1=2, n2=3, n3=2, n4=14, n5=2;
r) formula I: n1=2, n2=4, n3=2, n4=13, n5=2;
s) formula: n1=2, n2=5, n3=2, n4=12, n5=2;
t) formula I: n1=2, n2=6, n3=2, n4=11, n5=2;
u) formula I: n1=2, n2=7, n3=2, n4=10, n5=2;
v) formula I: n1=2, n2=8, n3=2, n4=9, n5=2;
w) formula I: n1=2, n2=9, n3=2, n4=8, n5=2;
x) formula I: n1=2, n2=10, n3=2, n4=7, n5=2;
y) formula I: n1=2, n2=11, n3=2, n4=6, n5=2;
z) formula I: n1=2, n2=12, n3=2, n4=5, n5=2;
aa) formula I: n1=2, n2=13, n3=2, n4=4, n5=2;
bb) formula I: n5=2, n2=14, n3=2, n4=3, n5=2;
cc) formula I: n1=2, n2=15, n3=2, n4=2, n5=2; and
dd) formula I: n1=2, n2=9, n3=3, n4=4, n5=2.

4. The oligomeric compound of claim 3, wherein $Nu_1$ and $Nu_5$ are, independently, 2'-modified nucleosides.

5. The oligomeric compound of claim 4 wherein each of the 2-modified nucleosides independently comprises a 2'-substituent group selected from O—$C_1$-$C_{12}$ alkyl, substituted O—$C_1$-$C_{12}$ alkyl, O—$C_2$-$C_{12}$ alkenyl, substituted O—$C_2$-$C_{12}$ alkenyl, O—$C_2$-$C_{12}$ alkynyl, substituted O—$C_2$-$C_{12}$ alkynyl, amino, substituted amino, amide, substituted amide, aralkyl, substituted aralkyl, O-aralkyl, substituted O-aralkyl, $N_3$, SH, CN, OCN, $CF_3$, $OCF_3$, $SOCH_3$, —$SO_2CH_3$, heterocycloalkyl, heterocycloalkaryl, aminoalkylamino and polyalkylamino; and wherein each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, O—$C_1$-$C_{12}$ alkyl, substituted O—$C_1$-$C_{12}$ alkyl, S—$C_1$-$C_{12}$ alkyl, substituted S—$C_1$-$C_{12}$ alkyl, acyl (C(=O)—H), substituted acyl, amino, substituted amino, amide, substituted amide, $C_1$-$C_{12}$ alkylamino, substituted $C_1$-$C_{12}$ alkylamino, $C_1$-$C_{12}$ aminoalkoxy, substituted $C_1$-$C_{12}$ aminoalkoxy, $C_1$-$C_{12}$ alkylaminooxy, substituted $C_1$-$C_{12}$ alkylaminooxy, guanidinyl, substituted guanidinyl or a protecting group.

6. The oligomeric compound of claim 5 wherein each 2'-substituent group is independently selected from O—$C_1$-$C_{12}$ alkyl, O—$CH_2$—$CH_2$—$CH_2$—$NH_2$, O—$(CH_2)_2$—O—$N(R_6)2$, O—$CH_2C$(=O)—$N(R_6)_2$, O—$(CH_2)_2$—O—$(CH_2)_2$—$N(R_6)_2$, O—$CH_2$—$CH_2$—$CH_2$—$NHR_6$, $N_3$, O—$CH_2$—CH=$CH_2$, $NHCOR_6$ or O—$CH_2$—N(H)—C(=$NR_6$)[$N(R_6)_2$];

wherein each $R_6$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl or a protecting group wherein the substituent groups are halogen, hydroxyl, amino, azido, cyano, haloalkyl, alkenyl, alkoxy, thioalkoxy, haloalkoxy or aryl.

7. The oligomeric compound of claim 5 wherein each 2'-substituent group is, independently, $O(CH_2)_{0-2}CH_3$, $O(CH_2)_2OCH_3$, $O(CH_2)_2SCH_3$, $OCH_2C(H)CH_2$, $O(CH_2)_2ON(CH_3)_2$ or $OCH_2C$(=O)$N(H)CH_3$.

8. The oligomeric compound of claim 7 wherein each 2'-substituent group is, independently, $OCH_3$ or O—$(CH_2)_2$—$OCH_3$.

9. The oligomeric compound of claim 8 wherein each 2'-substituent group is O—$(CH_2)_2$—$OCH_3$.

10. The oligomeric compound of claim 4, wherein the 2'-modified nucleoside is a bicyclic sugar modified nucleoside.

11. The oligomeric compound of claim 10, wherein each bicyclic sugar modified nucleoside independently comprises a D or L sugar in the alpha or beta configuration.

12. The oligomeric compound of claim 10 wherein each of the bicyclic sugar modified nucleosides independently comprises a bridge group between the 2' and the 4'-carbon atoms comprising from 1 to 8 linked biradical groups independently selected from —O—, —S—, —N($R_1$)—, —C($R_1$)($R_2$)—, —C($R_1$)=C($R_1$)—, —C($R_1$)=N—, —C(=$NR_1$)—, —Si($R_1$)($R_2$)—, —S(=O)$_2$—, —S(=O)—, —C(=O)— and —C(=S)—;

each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and wherein each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

13. The oligomeric compound of claim 10 wherein each bicyclic sugar modified nucleoside independently comprises from 1 to 4 of the linked biradical groups.

14. The oligomeric compound of claim 10 wherein each bicyclic sugar modified nucleoside independently comprises 2 or 3 of the linked biradical groups.

15. The oligomeric compound of claim 10 wherein each bicyclic sugar modified nucleoside comprises 2 of the linked biradical groups.

16. The oligomeric compound of claim 12 wherein each bridge group is, independently, —$CH_2$—, —$(CH_2)_2$—, —$CH_2$—O—, —$(CH_2)_2$—O— or —$CH_2$—N($R_3$)—O— wherein $R_3$ is H or $C_1$-$C_{12}$ alkyl.

17. The oligomeric compound of claim 12 wherein each bridge group is, independently, —$CH_2$—O— or —$(CH_2)_2$—O—.

18. The oligomeric compound of claim 2, wherein $Nu_1$ is O—$(CH_2)_2$—$OCH_3$, $Nu_3$ is O—$(CH_2)_2$—$OCH_3$, $Nu_5$O—$(CH_2)_2$—$OCH_3$, $T_1$ is H and $T_2$ is H, and wherein formula I is selected from:
  a. formula I: n1=2, n2=19, n3=0, n4=0, n5=2;
  b. formula I: n1=2, n2=2, n3=3, n4=14, n5=2;
  c. formula I: n1=2, n2=5, n3=3, n4=11, n5=2;
  d. formula I: n1=2, n2=8, n3=3, n4=8, n5=2;
  e. formula I: n1=2, n2=11, n3=3, n4=5, n5=2;
  f. formula I: n1=2, n2=14, n3=3, n4=2, n5=2;
  g. formula I: n1=2, n2=9, n3=3, n4=7, n5=2;
  h. formula I: n1=2, n2=10, n3=3, n4=6, n5=2;
  i. formula I: n1=2, n2=12, n3=3, n4=4, n5=2;
  j. formula I: n1=2, n2=3, n3=3, n4=13, n5=2;
  k. formula I: n1=2, n2=4, n3=3, n4=12, n5=2;
  l. formula I: n1=2, n2=6, n3=3, n4=10, n5=2;
  m. formula I: n1=2, n2=7, n3=3, n4=9, n5=2;
  n. formula I: n1=2, n2=13, n3=3, n4=3, n5=2;
  o. formula I: n1=2, n2=8, n3=6, n4=5, n5=2;
  p. formula I: n1=2, n2=2, n3=2, n4=15, n5=2;
  q. formula I: n1=2, n2=3, n3=2, n4=14, n5=2;
  r. formula I: n1=2, n2=4, n3=2, n4=13, n5=2;
  s. formula I: n1=2, n2=5, n3=2, n4=12, n5=2;
  t. formula I: n1=2, n2=6, n3=2, n4=11, n5=2;
  u. formula I: n1=2, n2=7, n3=2, n4=10, n5=2;
  v. formula I: n1=2, n2=8, n3=2, n4=9, n5=2;
  w. formula I: n1=2, n2=9, n3=2, n4=8, n5=2;
  x. formula I: n1=2, n2=10, n3=2, n4=7, n5=2;
  y. formula I: n1=2, n2=11, n3=2, n4=6, n5=2;
  z. formula I: n1=2, n2=12, n3=2, n4=5, n5=2;
  aa. formula I: n1=2, n2=13, n3=2, n4=4, n5=2;
  bb. formula I: n5=2, n2=14, n3=2, n4=3, n5=2;
  cc. formula I: n1=2, n2=15, n3=2, n4=2, n5=2; and
  dd. formula I: n1=2, n2=9, n3=3, n4=4, n5=2.

19. The oligomeric compound of claim 18 wherein the oligomeric compound comprises at least one phosphorothioate internucleoside linkage.

20. The oligomeric compound of claim 1 wherein each internucleoside linkage comprises a phosphorothioate internucleoside linkage.

* * * * *